United States Patent
Smith

[11] Patent Number: 5,848,590
[45] Date of Patent: Dec. 15, 1998

[54] TRACHEOSTOMA FILTER WITH HME PROPERTIES

[75] Inventor: Rory James Maxwell Smith, Yorkshire, United Kingdom

[73] Assignee: Kapitex Healthcare Limited, Wetherby, United Kingdom

[21] Appl. No.: 800,557

[22] Filed: Feb. 18, 1997

[51] Int. Cl.⁶ .............................. A62B 18/08; A62B 7/10; A62B 23/02; A61M 16/00
[52] U.S. Cl. ................................ 128/201.13; 128/205.27; 128/207.16
[58] Field of Search ................... 128/207.14–207.17, 128/911, 912, DIG. 26, 205.27, 205.29, 206.14, 204.13, 201.13, 206.15–206.17, 206.11, 206.12, 207.12

[56] References Cited

U.S. PATENT DOCUMENTS

| | | | |
|---|---|---|---|
| 3,747,597 | 7/1973 | Olivera | 128/206.11 |
| 3,920,009 | 11/1975 | Olsen . | |
| 4,004,584 | 1/1977 | Geaney | 128/206.14 |
| 4,240,420 | 12/1980 | Riaboy | 128/206.14 |
| 4,382,440 | 5/1983 | Kapp et al. . | |
| 4,463,757 | 8/1984 | Schmidt . | |
| 4,687,482 | 8/1987 | Hanson . | |
| 4,883,052 | 11/1989 | Weiss et al. . | |
| 4,971,054 | 11/1990 | Andersson et al. . | |
| 5,022,394 | 6/1991 | Chmielinski . | |
| 5,119,809 | 6/1992 | Gerson | 128/203.11 |
| 5,186,165 | 2/1993 | Swann . | |

FOREIGN PATENT DOCUMENTS

| | | | |
|---|---|---|---|
| 294 707 | 6/1988 | European Pat. Off. . | |
| 0413127 | 7/1990 | European Pat. Off. | 128/201.13 |
| 2 583 290 | 12/1986 | France . | |
| 37 33 389 | 4/1989 | Germany . | |
| 2 028 664 | 3/1980 | United Kingdom . | |
| 2 214 089 | 8/1989 | United Kingdom . | |
| 2231509 | 11/1990 | United Kingdom | 128/201.13 |
| WO 91/05579 | 5/1991 | WIPO . | |
| WO 94/01158 | 1/1994 | WIPO . | |
| WO 94/01199 | 1/1994 | WIPO . | |

OTHER PUBLICATIONS

A.S. Jones, J.M. Lancer, J.C. Stevens, and E. Beckingham, Nasal resistance to airflow (its measurement, reproducibility and normal parameters, *The Journal of Laryngology and Otology*, Aug. 1987, vol. 101, pp. 800–808.

*Primary Examiner*—Kimberly L. Asher
*Attorney, Agent, or Firm*—Merchant, Gould, Smith, Edell, Welter & Schmidt

[57] ABSTRACT

A filter assembly for filtering air that is to be breathed through a tracheostoma comprises (a) a housing, and (b) a filter component which can be fitted into the housing the filter component is movable within the housing as a result of a pressure difference across the component due to breathing, between an inhalation position, and an exhalation position resulting in a change in resistance to breathing through the assembly.

13 Claims, 2 Drawing Sheets

TRACHEOSTOMA FILTER WITH HME PROPERTIES

BACKGROUND TO THE INVENTION

This invention relates to a filter assembly for filtering air that is to be breathed through a tracheostoma, for example in patients who have received a tracheostomy, for example as part of a laryngectomy. Under such circumstances, the assembly can be fitted over a tracheostoma, or to a tracheostomy tube.

It is known to provide a filter over a tracheostoma which can help to simulate some of the natural functions of the nose, for example to filter air, to exchange heat and moisture between inhaled and exhaled air, and to impart resistance to breathing. Resistance to breathing has been found to give rise to benefits in terms of improving the tone of muscles associated with breathing and, consequently, improved resistance to infection in the patient. This can be particularly advantageous in a patient recovering from an operation and having to adapt from normal nasal breathing to breathing through a tracheostoma.

Resistance to passage of air through a filter positioned over a tracheostoma can give rise to discomfort for a user, and possibly also to danger, when it is desired to expel large amounts of air, for example during coughing or sneezing, and possibly also if the filter becomes blocked by mucus or phlegm. Inability to release the increased pressure by breathing through the filter, in these and similar situations, can lead to the user trying to remove the filter from the tracheostoma. Failure to remove the filter can cause severe distress and, in extreme situations, lead to suffocation.

SUMMARY OF THE INVENTION

The present invention provides a filter assembly in which a filter component can move in a filter housing between inhalation and exhalation positions as a result of breathing leading to a change in the resistance to flow of air through the assembly, generally by a reduction in breathing resistance on exhalation.

Accordingly, in one aspect, the invention provides a filter assembly for filtering air that is to be breathed through a tracheostoma, which comprises (a) a housing, and (b) a filter component which can be fitted into the housing, the filter component being movable within the housing as a result of a pressure difference across the component due to breathing, between an inhalation position, and an exhalation position resulting in a change in resistance to breathing through the assembly.

Preferably, the resistance to breathing through the assembly is greater when the filter component is in the inhalation position than when it is in the exhalation position. It should however be understood that the assembly might for some applications be arranged so that the resistance is greater when the filter component is in the exhalation position, and subsequent discussion of the assembly arranged for greater resistance on exhalation is applicable in places also to the reverse arrangement.

The assembly of the invention has the advantage that a user of the assembly is able to expel large quantities of air such as when it is necessary to cough or to sneeze, or when the filter becomes at least partially blocked with mucus or phlegm. However, this ability is coupled with breathing resistance which is maintained during inhalation and, at least partially, during exhalation. This maintains the advantages that can be attained from the use of a filter, including filtration of inhaled air, exchange of heat and moisture between inhaled and exhaled air, and, in particular, resistance to breathing resulting in improvement in the tone of muscles associated with breathing. This can lead to improved pulmonary function and tissue oxygenation for the user, and further clinical benefits in terms of resistance to chest infection can follow. The assembly of the invention therefore represents a considerable improvement in convenience for the user in that, in many situations in which it is necessary to expel relatively large quantities of air, this can be achieved without having to remove the filter from the tracheostoma (although it must however be remembered that, in severe circumstances, removal of the filter can still be appropriate).

It will generally be appropriate for the filter component to move between the inhalation and exhalation positions by sliding in the housing along the breathing axis (being the axis through the assembly along which air generally flows from the environment towards the stoma). Preferably, the movement of the filter component from the inhalation position to the exhalation position results in the opening of leak channels through which exhaled air can leave the assembly, other than by passing through the filter. The leak channels will generally be between the filter component and a surface of the housing which the filter component engages when the resistance to breathing through the assembly is relatively high.

Preferably, the leak channels are arranged to open progressively so that the change in resistance to breathing through the assembly changes as a result of increased movement of the filter component in the housing. The progressive opening of leak channels can be arranged by arranging for the space between surfaces on the filter component and the housing which are in contact (so as, for some applications, to create a seal) when the filter component is in its high resistance position to get gradually larger as the filter component moves towards the low resistance position. For example, one or both of the said surfaces may be inclined to the breathing axis. This can result in leak channels that are tapered when viewed in cross-section, so that the volume of air that can pass through the channels increases as the displacement of the filter component, from the inhalation position when that is the high breathing resistance position, increases. This can have the advantage of enabling the reduction in breathing resistance that results from movement of the filter component to change according to the quantity of air that has to pass through the assembly. It means that the assembly can accommodate changes in the resistance to passage to air through the filter component as it becomes blocked by mucus or phlegm, providing a relatively constant resistance to breathing (at least on one of inhalation and exhalation, generally exhalation) through the assembly considered as a whole. This can be achieved by controlling the resistance to movement of the filter component in the housing between the inhalation and exhalation positions.

Preferably, the housing includes means for controlling the movement of the filter component between the inhalation and exhalation positions. For example, the movement can be controlled by means of a lug $8x$ on one of the housing and the filter component which slidingly engages a groove $8y$ on the other of the housing and the filter component. The lug and groove can for example be provided by axially extending castellations on the housing and a set of corresponding laterally projecting lugs on the filter component which fit into the castellations and can move axially within the castellations. Control means can help to ensure that the filter remains properly aligned throughout its movement between the inhalation and exhalation positions, helping to control the change in breathing resistance as a result of the movement. Means for controlling the movement of the filter component between the inhalation and exhalation positions can also provide resistance to movement of the filter component, for example by frictional effects between the filter component and the housing provided by the formations on the component and the housing, or by making the filter component appropriate massive so that the resistance to movement is provided by an inertia effect.

The housing of the assembly can be arranged for attachment to the skin of a patient around the stoma by means of an adhesive. A device which includes a filter housing and a filter, which is attached to the skin around a tracheostoma by means of adhesive, is disclosed in WO-A-94/01199. Subject matter disclosed in that document is incorporated in the specification of the present application by this reference. For example, the housing is mounted on an adhesive backed patch.

The housing can be arranged for mounting on a tracheal tube. An appropriate arrangement for attaching a filter assembly onto a tracheal tube is disclosed in WO-A-94/01158. Subject matter disclosed in that document is incorporated in the specification of the present application by this reference.

Preferably, the resistance to air flow through the filter component is at least about 0.1 $kPa.s.l^{-1}$, more preferably at least about 0.2 $kPa.s.l^{-1}$, especially at least about 0.4 $kPa.s.l^{-1}$. Preferably, the resistance is not more than about 2.0 $kPa.s.l^{-1}$, more preferably not more than about 1.5 $kPa.s.l^{-1}$, especially not more than about 1.0 $kPa.s.l^{-1}$. Resistance to air flow in breathing can be measured using rhinomanometry, for example as disclosed in Journal of Laryngology and Orology, August 1987, vol 101, pp 800 to 808. When resistance to air flow breathed through a tracheostoma is to be measured, the method is modified by inserting the tube of the rhinomanometer into the tracheostoma under the edge of a filter device, where it is sealed using a grommet. A mask is placed over the tracheostoma and the filter device. The pressure gradient across the filter device is determined by measuring the pressures inside and outside the filter device, respectively. The resistance to air flow can then be calculated as described in the paper.

The degree to which the resistance to breathing through the assembly changes when the filter component moves between inhalation and exhalation positions will depend on a number of factors, including for example the condition of the user of the assembly, the resistance to breathing provided by the assembly when the filter component is in the high resistance position (generally the inhalation position), and whether the movement of the filter component in the housing is progressive from the high breathing resistance position to the low breathing resistance position. It will generally be preferred for the amount of air to pass through the filter assembly other than through the filter component when the component is in the low resistance position to be at least about 5% (measured by volume), more preferably at least about 10%, especially at least about 12%. It will generally be preferred for that amount of air to be not more than about 30%, more preferably not more than about 20%, especially not more than about 17%.

Preferably, the filter component comprises a fabric and a supporting frame which extends around the fabric, in which the fabric is mounted, the filter component engaging the housing when fitted therein by means of the supporting band. As disclosed in WO-A-94/01199 referred to above, the filter component can comprise a laminate of more than one fabric, for example of fibres of a hydrophillic material, or of carbon fibres. The fabric can be mounted in the supporting frame as a result of moulding the frame in situ around the fabric. Lugs, grooves or other formations provided on the filter component to control its movement in the housing, or to provide resistance to that movement, can be formed as part of that moulding process.

INTRODUCTION OF THE DRAWINGS

FIG. 1 is a front elevation view of a filter assembly according to the invention, FIG. 2 is a sectional elevation through the assembly shown in FIG. 1, FIG. 3 is an exploded view of a filter comprising a laminate of layers of filter fabric material, and FIG. 4 is a cross-sectional view of a further embodiment of filter assembly in which the leak channel is tapered.

DESCRIPTION OF PREFERRED EMBODIMENTS

Figure 1:
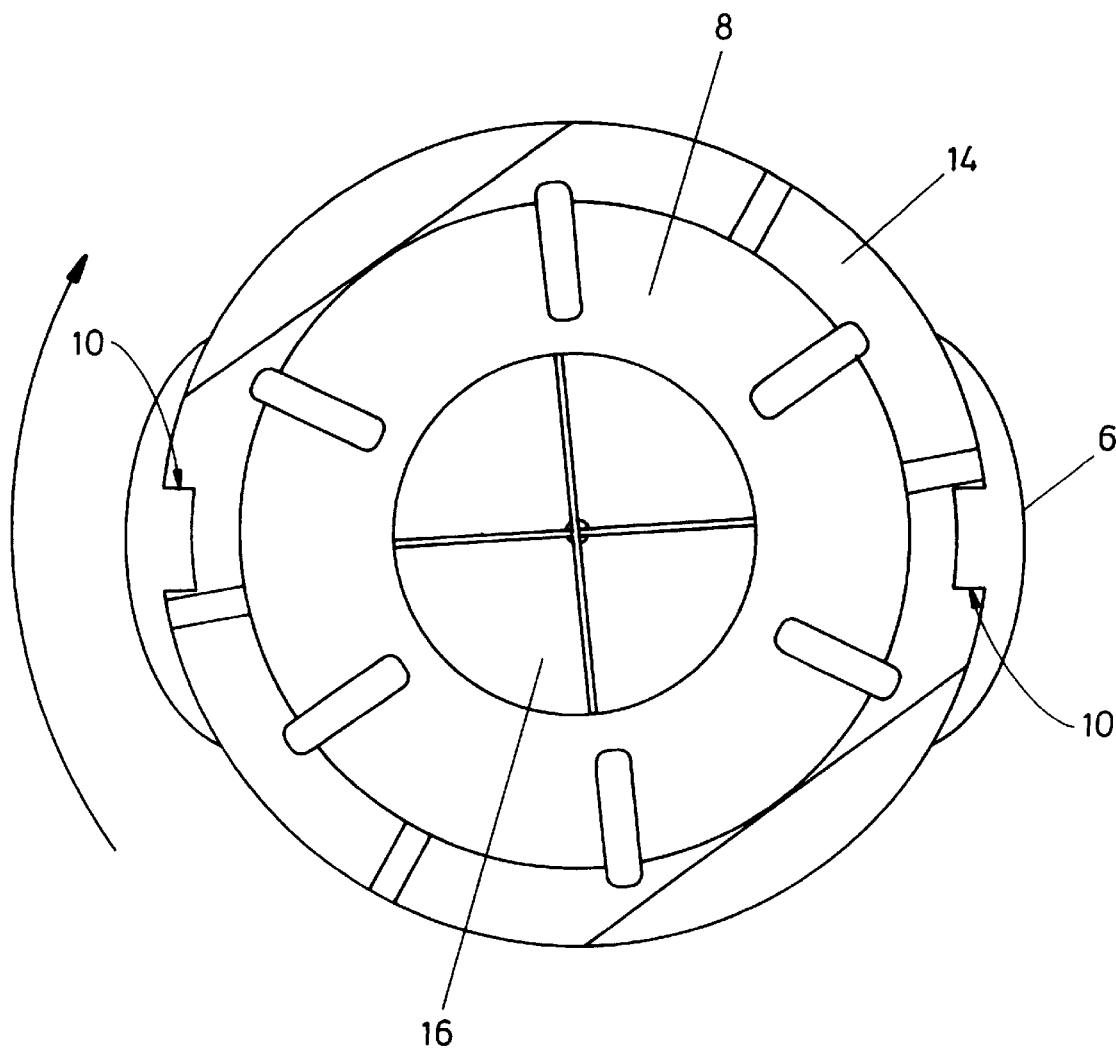
Figure 2:
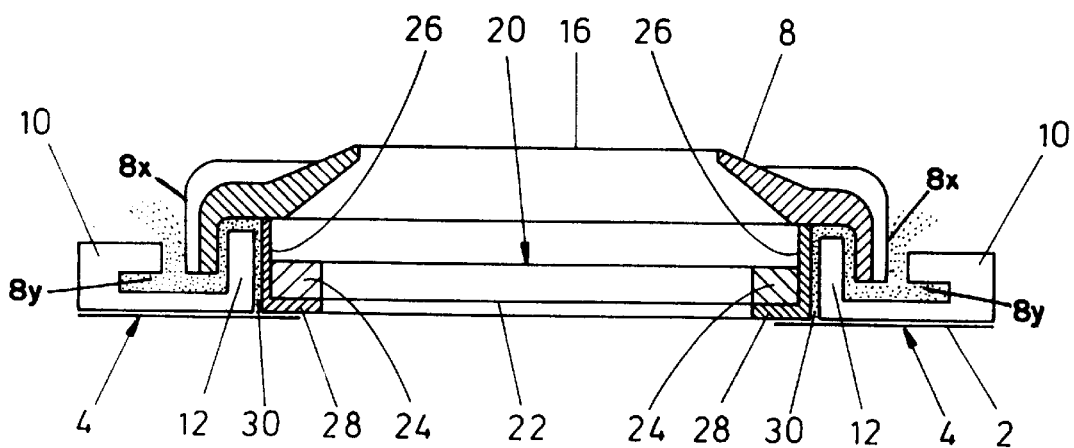
Figure 3:
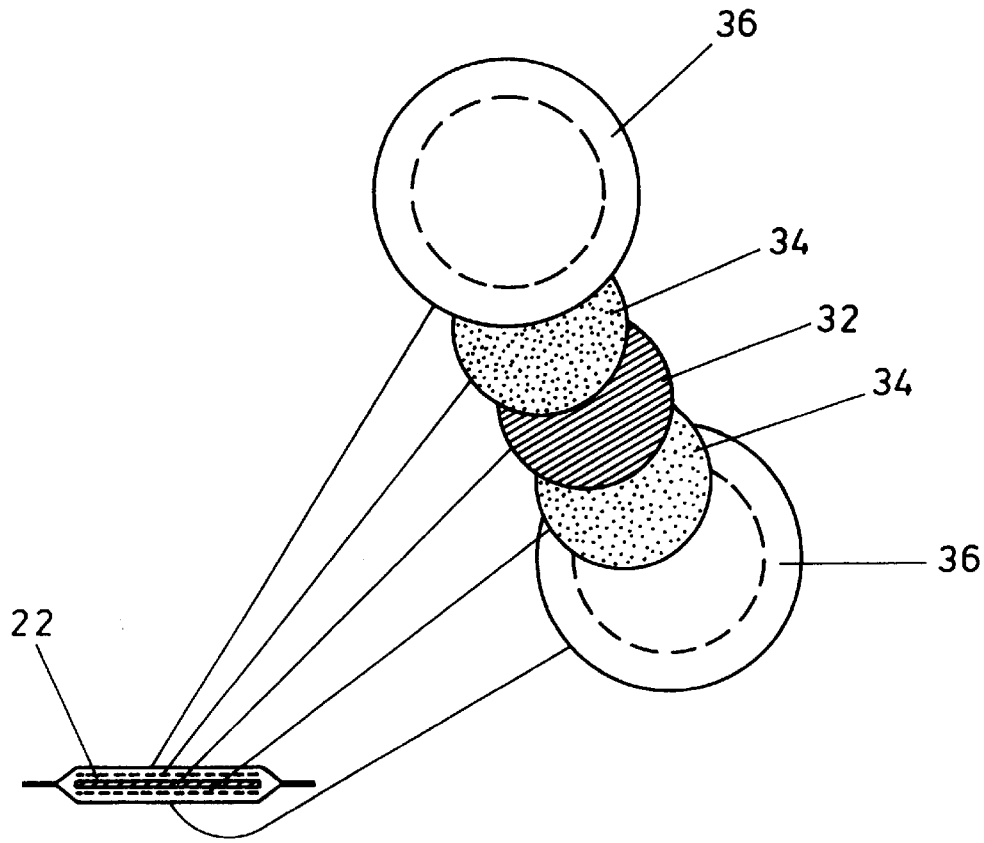
Figure 4:
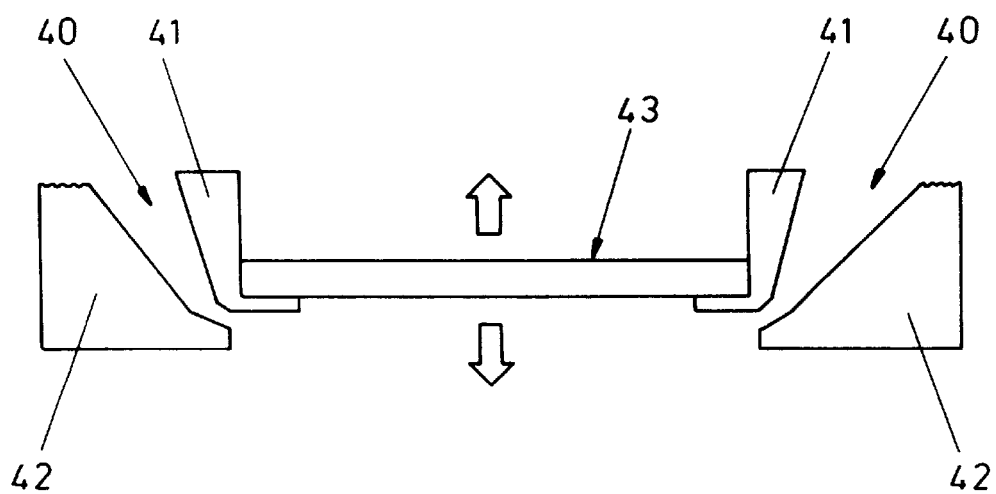

The illustrated filter assembly comprises a base plate 2 with an adhesive backing layer 4 by which the assembly can be fastened in place to the skin around a stoma. A suitable adhesive might comprise for example a hydrocolloid composition.

The housing for the filter component is located on the base plate 2. It comprises a base portion 6 and a cap 8, both formed from polymeric material by moulding. Suitable polymeric materials for the base portion and the cap of the housing include, for example, polyolefins such as polyethylene or polypropylene, polycarbonates, polyesters, polyamides and so on. The base portion of the housing has a pair of upstanding flange portions 10 on it. The base portion also has an upstanding ring 12 for engaging the filter component. The base portion of the housing is substantially circular and its transverse dimension at the widest point (where the flange portions are located) is about 40 mm.

The cap 8 has a laterally extending flange 14 arranged around most of its periphery, which can be received under the flange portions 10 on the base portion, in the manner of a bayonet fitting. The cap has an opening 16 at the outside of the assembly, which can be occluded when desired by means of the user's thumb, for example to operate a speech prosthesis.

The filter component 20 comprises one or more layers of a filter fabric 22, for example a layer of a polyester fabric impregnated with carbon 32, layers 34 of a non-woven fabric formed from a blend of polyester and viscose, and cover layers 36, for example a non-woven fabric made from polyolefin fibres (especially coextruded polypropylene and polyethylene). The fabric layers are held in a supporting frame 24 which is moulded in situ onto the fabric. The supporting frame is substantially circular when viewed in plan, with a diameter of about 25 mm.

The supporting frame 24 of the filter component 20 has an upstanding ring 26 extending in a direction when the assembly is in use towards the outside of the assembly away from the user's stoma. A lateral flange 28 is provided on the ring 26.

In order to construct the assembly, the filter component 20 is positioned within the base portion 6 of the housing with the lateral flange 28 on the upstanding ring 12 on the base portion. The engagement of the flange with the ring prevents the filter component from being inserted into the housing too far, and possibly entering the user's stoma. The filter component is retained in the housing by fastening the cap 8 of the housing onto the base portion 6 by means of the bayonet type fitting described above.

When the cap and the base portion tightly engage one another, the lateral flange 28 on the filter component is a loose fit between the cap and the upstanding ring 12 on the base portion. In use, when the user inhales, the filter component is drawn inwardly so that the lateral flange engages the ring. In this position, inhaled air is drawn substantially exclusively through the filter fabric layers 22, which provide filtration, heat and moisture exchange and resistance to breathing. When air is exhaled, the filter component is forced outwardly, opening a leak channel 30 from the assembly between the base portion of the housing and the cap, through which exhaled air can escape. The leak channel opens progressively as the filter component is displaced from the inhalation, high breathing resistance, position. The movement of the filter component is restricted by friction between the upstanding ring 12 on the base portion of the housing and the upstanding ring 26 on the filter component. The friction between these two rings ensures that the displacement of the filter component from the inhalation position is dependent on the pressure differential across the filter fabric layers 22. In another embodiment the surfaces of the upstanding rings 41, 42 are inclined to the breathing axis in order to define leak channels 40 which are tapered. In this arrangement, a relatively small outward movement of the filter 43 during exhalation produces a large in leakage path on movement.

What is claimed is:

1. A filter assembly for filtering air that is to be breathed through a tracheostoma, comprising:
    a housing;
    a filter component which can be fitted into the housing, the filter component being movable within the housing as a result of a pressure difference across the component due to breathing, between an inhalation position, and an exhalation position resulting in a change in resistance to breathing through the assembly;
    wherein the housing includes means for controlling the movement of the filter component between the inhalation and exhalation positions; and
    wherein the means for controlling the movement of the filter component comprises a lug on one of the housing and the filter component which slidingly engages a groove on the other of the housing and the filter component.

2. A filter assembly as claimed in claim 1, in which the resistance to breathing through the assembly is greater when the filter component is in the inhalation position than when it is in the exhalation position.

3. A filter assembly as claimed in claim 1, in which the filter component moves between the inhalation and exhalation positions by sliding in the housing along a breathing axis.

4. A filter assembly as claimed in claim 1, in which movement of the filter component from the inhalation position to the exhalation position results in an opening of leak channels through which exhaled air can leave the assembly, other than by passing through the filter.

5. A filter assembly as claimed in claim 4, in which the leak channels are arranged to open progressively so that the change in resistance to breathing through the assembly changes as a result of increased movement of the filter component in the housing.

6. A filter assembly as claimed in claim 5, tapered when viewed in cross-section, so that the volume of air that can pass through the channels increases as the displacement of the filter component increases.

7. A filter assembly as claimed in claim 1, in which the housing is arranged for attachment to the skin of a patient around the stoma by means of an adhesive.

8. A filter assembly as claimed in claim 7, in which the housing is mounted on an adhesive backed patch.

9. A filter assembly as claimed in claim 1, in which the housing is arranged for mounting on a tracheal tube.

10. A filter assembly as claimed in claim 1, in which the resistance to air flow through the filter component is at least about $0.1 \text{ kPa.s.l}^{-1}$.

11. A filter assembly as claimed in claim 10, in which the resistance to air flow through the filter component is at least about $0.2 \text{ kPa.s.l}^{-1}$.

12. A filter assembly as claimed in claim 1, in which the filter component comprises a fabric and a supporting frame which extends around the fabric, in which the fabric is mounted, the filter component engaging the housing when fitted therein by means of the supporting frame.

13. A filter assembly as claimed in claim 1, in which the housing includes means for attaching the assembly to the tracheostoma.

* * * * *

UNITED STATES PATENT AND TRADEMARK OFFICE
CERTIFICATE OF CORRECTION

PATENT NO. : 5,848,590

DATED : DECEMBER 15, 1998

INVENTOR(S) : SMITH

It is certified that error appears in the above-identified patent and that said Letters Patent is hereby corrected as shown below:

Front page, [56] References Cited, Foreign Patent Documents: insert —WO 93/08860 5/1993 WIPO—

Front page, [57] Abstract, line 3: "housing the" should read —housing. The—

Col. 3, line 9: "appropriate" should read —appropriately—

Col. 3, line 34: "Orology" should read —Otology—

Col. 4, line 10: "OF" should read —TO—

Col. 4, line 11: "elevation" should read —elevational—

Signed and Sealed this

Sixth Day of June, 2000

Q. TODD DICKINSON

*Attest:*

*Attesting Officer*     *Director of Patents and Trademarks*